United States Patent
Kim et al.

(10) Patent No.: US 10,788,493 B2
(45) Date of Patent: Sep. 29, 2020

(54) COMPOSITION FOR DIAGNOSING INFECTIOUS DISEASES OR INFECTIOUS COMPLICATIONS BY USING TRYPTOPHANYL-TRNA SYNTHETASE AND METHOD FOR DETECTING DIAGNOSTIC MARKER

(71) Applicant: JW BIOSCIENCE, Chungju-si (KR)

(72) Inventors: Sunghoon Kim, Seoul (KR); Mi Rim Jin, Seoul (KR); Young Ha Ahn, Daejeon (KR)

(73) Assignee: JW BIOSCIENCE, Chungju-si, Chungcheongbuk-Do (KR)

( * ) Notice: Subject to any disclaimer, the term of this patent is extended or adjusted under 35 U.S.C. 154(b) by 31 days.

(21) Appl. No.: 15/908,568

(22) Filed: Feb. 28, 2018

(65) Prior Publication Data
US 2018/0275127 A1    Sep. 27, 2018

Related U.S. Application Data

(63) Continuation-in-part of application No. PCT/KR2016/009802, filed on Sep. 1, 2016.

(30) Foreign Application Priority Data

Sep. 1, 2015 (KR) .................. 10-2015-0123743
Mar. 2, 2016 (KR) .................. 10-2016-0025329

(51) Int. Cl.
| | | |
|---|---|---|
| G01N 33/53 | (2006.01) | |
| G01N 33/573 | (2006.01) | |
| C12Q 1/689 | (2018.01) | |
| C12Q 1/68 | (2018.01) | |
| C12Q 1/6883 | (2018.01) | |
| C07K 16/40 | (2006.01) | |
| C12Q 1/6813 | (2018.01) | |
| C12Q 1/70 | (2006.01) | |

(52) U.S. Cl.
CPC .......... *G01N 33/573* (2013.01); *C07K 16/40* (2013.01); *C12Q 1/68* (2013.01); *C12Q 1/689* (2013.01); *C12Q 1/6813* (2013.01); *C12Q 1/6883* (2013.01); *C12Q 1/701* (2013.01); *C12Y 601/01002* (2013.01); *C12Q 2600/112* (2013.01); *C12Q 2600/118* (2013.01); *C12Q 2600/158* (2013.01); *G01N 2333/9015* (2013.01); *G01N 2800/26* (2013.01); *G01N 2800/56* (2013.01); *Y02A 50/59* (2018.01)

(58) Field of Classification Search
None
See application file for complete search history.

(56) References Cited

U.S. PATENT DOCUMENTS

| | | | |
|---|---|---|---|
| 5,851,809 A | 12/1998 | Lawlor | |
| 2011/0014614 A1 | 1/2011 | Liew | |
| 2013/0273045 A1* | 10/2013 | Watkins | ............... A61K 38/53 424/134.1 |
| 2013/0330312 A1* | 12/2013 | Greene | ............... A61K 38/53 424/94.3 |
| 2015/0133469 A1 | 5/2015 | O'Garra et al. | |

FOREIGN PATENT DOCUMENTS

| | | |
|---|---|---|
| EP | 0843014 A2 | 5/1998 |
| JP | H10215882 A | 8/1998 |
| JP | 2011526152 A | 10/2011 |
| KR | 20150077891 | 7/2015 |
| WO | WO 2009/158521 A2 | 12/2009 |
| WO | WO 2010090471 * | 5/2010 |
| WO | WO 2012/048125 | 4/2012 |
| WO | WO 2012/048125 A2 | 4/2012 |

OTHER PUBLICATIONS

NCBI, GenBank accession No. AAH95453.1, 'WRA protein [*Homo sapiens*]', 2005.
NCBI, GenBank accession No. BC017489.1, '*Homo sapiens* tryptophanyl-tRNA synthetase, mRNA (cDNA clon MGC: 15973, IMAGE: 3542671), complete cds', 2006.
Hjelm et al., "Exploring epitopes of antibodies toward the human tryptophanyl-tRNA synthetase", New Biotechnology, 2010, 27(2): 129-137.
Matsunaga et al., "Analysis of Gene Expression During Maturation of Immature Dendritic Cells Derived from Peripheral Blood Monocytes", Scandinavian Journal of Immunology, 2002, 56: 593-601.
Turpaev et al., "Alternative processing of the tryptophanyl-tRNA synthetase mRNA from interferon-treated human cells", Eur. J. Biochem., 1996, 240: 732-737.

(Continued)

*Primary Examiner* — Jennifer E Graser
(74) *Attorney, Agent, or Firm* — James S. Keddie; Bozicevic, Field & Francis LLP

(57) ABSTRACT

The present invention relates to a composition for diagnosing infectious diseases by using a tryptophanyl-tRNA synthase (WRS) and a method for detecting a diagnostic marker and, more specifically, to: a composition for diagnosing infectious diseases, containing a preparation measuring the WRS protein or mRNA expression level; a diagnostic kit; a method for detecting the WRS for providing information required for the diagnosis of infectious diseases, and a method for determining the infectious disease mortality risk by using the WRS. According to the present invention, the WRS is increased only in infection-induced infectious diseases, differentiating non-infectious diseases therefrom, and is rapidly increased in the early stage of infection. In addition, the level of the WRS is closely correlated with the severity and prognosis of diseases or complications induced by infection. Therefore, the WRS can be used as a marker for more rapid and accurate diagnosis, in comparison to a conventional marker for infectious diseases or complications thereof.

6 Claims, 9 Drawing Sheets

Specification includes a Sequence Listing.

(56) References Cited

OTHER PUBLICATIONS

Pennings et al., "Identification of a Common Gene Expression Response in Different Lung Inflammatory Diseases in Rodents and Macaques", PLoS One, 2008, 3(7): e2596.
GenBank: Accession No. AAH95453.1, "WARS protein [*Homo sapiens*]", 2005.
GenBank: Accession No. BC017489.1, "*Homo sapiens* tryptophanyl-tRNA synthetase, mRNA (cDNA clone MGC:15973 Image:3542671), complete cds", 2006.

* cited by examiner

COMPOSITION FOR DIAGNOSING INFECTIOUS DISEASES OR INFECTIOUS COMPLICATIONS BY USING TRYPTOPHANYL-TRNA SYNTHETASE AND METHOD FOR DETECTING DIAGNOSTIC MARKER

CROSS-REFERENCE TO RELATED APPLICATIONS

This application is a continuation-in-part of International Application No. PCT/KR2016/009802, file on Sep. 1, 2016, which claims benefit of priority to Korean Application No. 10-2015-0123743, filed on Sep. 1, 2015 and Korean Application No. 10-2016-0025329, filed on Mar. 2, 2016, which applications are incorporated by reference herein.

TECHNICAL FIELD

The present application claims priority from Korean Patent Application No. 10-2015-0123743, filed on Sep. 1, 2015 and Korean Patent Application No. 10-2016-0025329, filed on Mar. 2, 2016, the entire contents of which are incorporated herein by reference.

The present invention relates to a composition for diagnosing infectious diseases by using a tryptophanyl-tRNA synthase (WRS) and a method for detecting a diagnostic marker. More specifically, the present invention relates to a composition for diagnosing infectious diseases, comprising an agent for measuring the protein or mRNA expression level of WRS; a diagnostic kit; a method for detecting WRS for providing information required for the diagnosis of infectious diseases; and a method for determining the infectious disease mortality risk by using WRS.

BACKGROUND OF THE INVENTION

Infectious diseases are diseases that occur when foreign bodies such as bacteria, fungi, and viruses appear to five in in blood, body fluids, and tissues. Unless being correctly identified and properly treated, they may become life-threatening diseases. Although the prevalence rate of infectious diseases is generally decreased according to the improvement of hygiene level, the threat of infectious diseases, which may be fatal, is increasing by the abuse of antibiotics, increased use of immunosuppressive agents following transplantation, reduction of immunity due to chemotherapy, and increase in the number of patients with underlying diseases such as diabetes and hypertension.

Currently, the diagnostic tool for infection is a polymerase chain reaction (POR) to identify infected organs and direct microbial culture from blood and urine of patient, as well as empirical judgment of the clinician based on the patients symptoms. However, the results of microbial cultivation in the laboratory are mostly negative, and the PCR method has a time limit. The prohormone of calcitonin (POT) is elevated within the first three to four hours of infection in most bacterial and fungal infections, but a higher level of its change is caused by gram-negative bacteria than other pathogens. It is also unknown whether this hormonal level may be elevated by viral infection. Thus, although there have been considerable advances in detecting many microbes in infectious diseases through previous studies, diagnostic methods currently in use still require a great amount of labor with poor sensitivity and specificity.

In particular, infectious diseases are mostly accompanied by an inflammatory reaction at the site of infection, while some of them may cause systemic inflammatory reaction, leading to a fatal result. This systemic inflammatory reaction differs in a treatment method therefor depending on its cause. Thus, it is very important for proper treatment to rapidly identify and diagnose various systemic inflammatory responses induced by non-infectious causes and inflammatory responses induced by pathogen infection. It is important to initiate appropriate antibiotic treatment as soon as possible, especially since infectious inflammation caused by infectious diseases can lead to death. Thus, such a diagnosis is essential for the survival of a patient with acute infectious inflammation.

Currently, C-reactive protein (CRP) is being used as a common diagnostic marker for a variety of inflammatory diseases. However, CRP levels cannot be distinctively used for identifying infectious inflammation because its level increases in both non-infectious and infectious inflammatory diseases. Therefore, it is necessary to develop a diagnostic reagent that can rapidly identify inflammation caused by infection.

DETAILED DESCRIPTION OF THE INVENTION

Technical Problem

Accordingly, the present inventors have completed the present invention after they have found that the expression level of a tryptophanyl-tRNA synthetase (TrpRS or WRS, hereinafter referred to as "WRS") rapidly increases from the early stage of infection due to infection by bacteria, viruses or fungi and in particular, the level of the WRS significantly increases compared with that of a healthy subject when an infectious inflammatory disease is involved, and that a non-infectious inflammatory disease is not associated with the level of WRS, suggesting that the level of WRS may be used as a marker for rapidly and accurately diagnosing an infectious disease and its complications.

Accordingly, an aspect of the present invention is to provide a composition for the diagnosis of an infectious disease, the composition comprising an agent for measuring the protein or mRNA expression level of tryptophanyl-tRNA synthetase.

Another aspect of the present invention is to provide a kit for diagnosing an infectious disease, the kit comprising an agent for measuring the protein or mRNA expression level of tryptophanyl-tRNA synthetase.

Another aspect of the present invention is to provide a method for detecting tryptophanyl-tRNA synthetase in a subject in need of obtaining information necessary for the diagnosis of an infectious disease, the method comprises:
(a) providing a sample of a subject;
(b) measuring the expression level of tryptophanyl-tRNA synthetase in the sample; and
(c) comparing the level of tryptophanyl-tRNA synthetase in the subject with the level of a healthy subject, and determining that the subject having an increased expression level of tryptophanyl-tRNA synthetase compared to the healthy subject has been infected with the infectious disease.

Still another aspect of the present invention is to provide a composition for determining the mortality risk of an infectious disease, the composition comprising an agent for measuring the protein or mRNA expression level of tryptophanyl-tRNA synthase.

Still another aspect of the present invention is to provide a method for determining the mortality risk of a subject afflicted with an infectious disease, the method comprising:
(a) providing a sample of a subject;
(b) measuring the expression level of tryptophanyl-tRNA synthetase in the sample; and
(c) determining that the mortality risk of the subject increases proportionally to an increase in the level of tryptophanyl-tRNA synthetase.

Further aspect of the present invention is to provide use of an agent for measuring the protein or mRNA expression level of tryptophanyl-tRNA synthetase for preparing an agent for the diagnosis of an infectious disease.

Further aspect of the present invention is to provide a method for diagnosing an infectious disease in a subject in need thereof, the method comprising measuring the protein or mRNA expression level of tryptophanyl-tRNA synthetase in a sample of a subject in need thereof.

Further another aspect of the present invention is to provide use of an agent for measuring the protein or mRNA expression level of tryptophanyl-tRNA synthetase for preparing an agent for determining the mortality risk of a subject afflicted with an infectious disease.

Technical Solution

An embodiment according to an aspect of the present invention provides a composition for the diagnosis of an infectious disease, the composition comprising an agent for measuring the protein or mRNA expression level of tryptophanyl-tRNA synthetase.

In addition, another embodiment according to the present invention provides a composition for the diagnosis of an infectious disease, the composition consisting of an agent for measuring the protein or mRNA expression level of tryptophanyl-tRNA synthetase.

In addition, another embodiment according to the present invention provides a composition for the diagnosis of an infectious disease, the composition consisting essentially of an agent for measuring the protein or mRNA expression level of tryptophanyl-tRNA synthetase.

An embodiment according to another aspect of the present invention provides a kit for diagnosing an infectious disease, the kit comprising an agent for measuring the protein or mRNA expression level of tryptophanyl-tRNA synthetase.

In addition, another embodiment according to the present invention provides a kit for diagnosing an infectious disease, the kit consisting of an agent for measuring the protein or mRNA expression level of tryptophanyl-tRNA synthetase.

In addition, another embodiment according to the present invention provides a kit for diagnosing an infectious disease, the kit consisting essentially of an agent for measuring the protein or mRNA expression level of tryptophanyl-tRNA synthetase.

An embodiment according to still another aspect of the present invention provides a method for detecting tryptophanyl-tRNA synthetase in a subject in need of obtaining information necessary for the diagnosis of an infectious disease, the method comprises:
(a) providing a sample of a subject;
(b) measuring the expression level of tryptophanyl-tRNA synthetase in the sample; and
(c) comparing the level of tryptophanyl-tRNA synthetase in the subject with the level of a healthy subject, and determining that the subject having an increased expression level of tryptophanyl-tRNA synthetase compared to the healthy subject has been infected with the infectious disease.

In addition, another embodiment according to the present invention provides a method for detecting tryptophanyl-tRNA synthetase in a subject in need of obtaining information necessary for the diagnosis of an infectious disease, the method consisting of:
(a) providing a sample of a subject;
(b) measuring the expression level of tryptophanyl-tRNA synthetase in the sample; and
(c) comparing the level of tryptophanyl-tRNA synthetase in the subject with the level of a healthy subject, and determining that the subject having an increased expression level of tryptophanyl-tRNA synthetase compared to the healthy subject has been infected with the infectious disease.

In addition, another embodiment according to the present invention provides a method for detecting tryptophanyl-tRNA synthetase in a subject in need of obtaining information necessary for the diagnosis of an infectious disease, the method consisting essentially of:
(a) providing a sample of a subject;
(b) measuring the expression level of tryptophanyl-tRNA synthetase in the sample; and
(c) comparing the level of tryptophanyl-tRNA synthetase in the subject with the level of a healthy subject, and determining that the subject having an increased expression level of tryptophanyl-tRNA synthetase compared to the healthy subject has been infected with the infectious disease.

An embodiment according to still another aspect of the present invention provides a composition for determining the mortality risk of an infectious disease, the composition comprising an agent for measuring the protein or mRNA expression level of tryptophanyl-tRNA synthase.

In addition, another embodiment according to the present invention provides a composition for determining the mortality risk of an infectious disease, the composition consisting of an agent for measuring the protein or mRNA expression level of tryptophanyl-tRNA synthase.

In addition, another embodiment according to the present invention provides a composition for determining the mortality risk of an infectious disease, the composition consisting essentially of an agent for measuring the protein or mRNA expression level of tryptophanyl-tRNA synthase.

An embodiment according to still another aspect of the present invention provides a method for determining the mortality risk of a subject afflicted with an infectious disease, the method comprising:
(a) providing a sample of a subject;
(b) measuring the expression level of tryptophanyl-tRNA synthetase in the sample; and
(c) determining that the mortality risk of the subject increases proportionally to an increase in the level of tryptophanyl-tRNA synthetase.

In addition, another embodiment according to the present invention provides a method for determining the mortality risk of a subject afflicted with an infectious disease, the method consisting of:
(a) providing a sample of a subject;
(b) measuring the expression level of tryptophanyl-tRNA synthetase in the sample; and
(c) determining that the mortality risk of the subject increases proportionally to an increase in the level of tryptophanyl-tRNA synthetase.

In addition, another embodiment according to the present invention provides a method for determining the mortality risk of a subject afflicted with an infectious disease, the method consisting essentially of:

(a) providing a sample of a subject;
(b) measuring the expression level of tryptophanyl-tRNA synthetase in the sample; and
(c) determining that the mortality risk of the subject increases proportionally to an increase in the level of tryptophanyl-tRNA synthetase.

An embodiment according to still further aspect of the present invention provides use of an agent for measuring the protein or mRNA expression level of tryptophanyl-tRNA synthetase for preparing an agent for the diagnosis of an infectious disease.

An embodiment according to still further aspect of the present invention provides a method for diagnosing an infectious disease in a subject in need thereof, the method comprising measuring the protein or mRNA expression level of tryptophanyl-tRNA synthetase in a sample of a subject in need thereof.

An embodiment according to still further aspect of the present invention is to provide use of an agent for measuring the protein or mRNA expression level of tryptophanyl-tRNA synthetase for preparing an agent for determining the mortality risk of a subject afflicted with an infectious disease.

Hereinafter, the present invention will be described in detail.

The present invention is to provide a composition for the diagnosis of an infectious disease, the composition comprising an agent for measuring the protein or mRNA expression level of tryptophanyl-tRNA synthetase.

The present inventors were the first to confirm that the expression level of the WRS rapidly increases from the early stage of infection due to infection by bacteria, viruses or fungi and it was significantly higher than that of a healthy control when symptoms such as pneumonia or sepsis appear as infectious complications.

Furthermore, the WRS expression level in sepsis patients is highly correlated with the severity and prognosis of sepsis, and because WRS is increased only in infectious inflammation, it is possible to quickly and accurately distinguish between infectious inflammatory disease and non-infectious inflammatory disease. Thus, it was confirmed that the value of a diagnostic marker in infectious complications is very high.

The inventors of the present invention have specifically confirmed the following in relation with the WRS and the diagnosis of infectious diseases.

According to one embodiment of the present invention, the WRS has been confirmed to greatly increase in infections caused by bacteria, viruses or fungi.

When human peripheral blood mononuclear cells (PBMC) are infected with *Salmonella typhimurium* or RSV or PR8 virus, the level of the WRS released from these PBMC to the outside of the cell rapidly increases within 1 hour after the infection. In addition, the amount of the WRS present in the serum of patients with viral pneumonia was increased compared to the healthy control.

In another embodiment of the present invention, it was confirmed that the amount of the WRS in the serum of a patient with sepsis or septic shock due to infection with bacteria or fungi was significantly increased compared with the serum of the healthy control.

GRS and KRS, which are different types of aminoacyl-tRNA synthetase (ARS) secreted outside the cell, were not different between sepsis patients and the healthy control, and the increase in the WRS due to infection was found to be specific to WRS, not to the general phenomenon of ARS.

There was no statistically significant difference in the increasing trend of the WRS in each sepsis patient due to the infections of Gram-negative bacteria, Gram-positive bacteria, and fungi, and thus it was confirmed that the WRS can be used effectively for diagnosis of sepsis due to the infections of gram-negative bacteria, gram-positive bacteria, and fungi. In addition, there was no significant difference of the WRS levels in blood between single infected and multiple infected patients, indicating that it can be used for diagnosis of sepsis due to single infections or multiple infections.

In particular, there was no statistically significant difference in the amount of the WRS in the serum of patients with autoimmune diseases such as systemic inflammation reactive symptom (SIRS), non-infective chronic inflammatory diseases such as asthma and rheumatoid arthritis, and Sjogren's syndrome compared to the healthy controls. Thus, the level of expression of the WRS was not increase in all inflammatory responses, but it was confirmed that it was specifically increased only in inflammatory responses induced by bacterial, viral or fungal infections. In addition, the level of the WRS was further increased in patients with septic shock than in patients with sepsis, so it was confirmed that the level of the WRS expression was also associated with the severity of sepsis. That is, it can be determined that the higher the expression level of the WRS is, the more severe the symptoms of sepsis can be.

In another embodiment of the present invention, it was confirmed by ROC curve analysis of the WRS that the WRS has excellent sensitivity and specificity in diagnosing inflammation caused by infection. In correlation to the severity of sepsis marked by SOFA score, the WRS was also found to have a higher correlation than CPR, an existing inflammation diagnostic marker. In other words, the higher the level of expression of WRSis, the higher the SOFA score is. Thus, it can be predicted that the probability of organ failure due to sepsis is high.

The WRSlevel in patients who died of sepsis after 28 days of sepsis diagnosis was significantly higher than that in surviving sepsis patients, further confirming that WRS has a high correlation with the severity of sepsis and prognosis. That is, as the level of expression of WRSincreases, it can be predicted that the severity of sepsis is higher and the prognosis is worse.

Also, serum samples from 120 healthy persons, 18 SIRS patients (due to causes other than infectious diseases), 166 sepsis patients and 160 septic shock patients were subjected to clinical studies and were compared with a conventionally used marker, procalcitonin. As a result, although the results of the WRSare correlated to the results of procalcitonin, the WRS was only detected specifically for the complications of infectious diseases and it was confirmed that it can select patients who are concerned about death.

Using the close correlation between the level of expression of the WRS described above and the severity of pneumonia and septicemia, it can be used as a diagnostic marker of sepsis which is more efficient than existing sepsis diagnosis markers. In particular, since the WRS increases specifically in sepsis and rapidly increases at the early stage of infection, it is possible to prevent the delay of the initial treatment due to unknown causes of inflammation and to allow the patient to receive the most suitable treatment by rapidly distinguishing between infectious inflammatory diseases such as sepsis and non-infectious inflammatory diseases.

Based on the discovery of the present inventors, the present invention provides a composition for the diagnosis of an infectious disease, the composition comprising an agent for measuring the protein or mRNA expression level of tryptophanyl-tRNA synthetase.

In the present invention, "WRS" means triptophanyl-tRNA synthetase, which is also known as tryptophan-tRNA ligase, TrpRS, and WARS. The WRS is an enzyme that mediates the aminoacylation reaction of tryptophan and tRNA. The WRS is encoded by the WARS gene in humans, and the amino acid sequence and mRNA nucleotide sequence of the protein are known as Genbank accession number NP_004175.2 (protein) and Genbank accession number NM_004184.3 (mRNA nucleotide sequence). The WRS has two isoforms: a cytoplasmic form (WARS or tryptophanyl-tRNA synthetase, cytoplasmic) and a mitochondrial form (WARS2 or tryptophanyl-tRNA synthetase, mitochondrial). The WRS in the present invention is preferably a cytoplasmic form.

In the present invention, 'expression' means that a protein or a nucleic acid is produced in a cell. "Protein" is used interchangeably with "polypeptide" or "peptide" and for example, refers to a polymer of amino acid residues as commonly found in natural state proteins. A "polynucleotide" or "nucleic acid" refers to deoxyribonucleotide (DNA) or ribonucleotide (RNA) in the form of single strand or double strands. Unless otherwise limited, it also includes known analogs of natural nucleotides that hybridize to nucleic acids in a manner similar to naturally occurring nucleotides. 'mRNA' is an RNA that transfers genetic information (gene-specific nucleotide sequence) to ribosomes that specify the amino acid sequence from a specific gene during protein synthesis. 'Diagnosis' means identifying the presence or characteristic of a pathological condition. The diagnosis in the present invention is to determine the expression level of the WRS gene, that is, the level of WRS protein or WRS mRNA is measured to ascertain pathological presence or disease of the infectious disease.

When the diagnostic composition of the present invention is to measure the expression level of WRS protein, the agent for measuring the expression level of WRS protein may be an antibody that specifically binds to the WRS protein.

The WRS protein may be derived from a mammal including a human, preferably the amino acid sequence represented by SEQ. ID NO: 1.

"Antibody" means immunoglobulin that specifically binds to an antigenic site. The antibody of the present invention does not react with other proteins containing this synthetic enzyme other than the WRS, and is an antibody which specifically binds only to the WRS protein. The WRS antibody can be produced by cloning the WRS gene into an expression vector to obtain a protein encoded by the gene and can be prepared from the obtained protein according to a conventional method in the art. A fragment of WRS protein including a WRS antigenic site may be used to prepare a WRS protein specific antibody. The form of the antibody of the present invention is not particularly limited and includes a polyclonal antibody or a monoclonal antibody. In addition, if it has an antigen-antibody binding property, some of the whole antibodies are also included in the antibodies of the present invention, and includes all kinds of immunoglobulin antibodies that specifically bind to the WRS. For example, it includes a full form antibody having two full-length light chains and two full-length heavy chains, as well as functional fragments of antibody molecules, that is, (Fab), $F(ab')_2$, $F(ab')_2$ and Fv having an antigen binding function. Further, the antibody of the present invention includes a specific antibody such as a humanized antibody, a chimeric antibody and a recombinant antibody as long as it can specifically bind to the WRS protein.

In the present invention, the WRS protein preferably comprises a human WRS amino acid sequence represented by SEQ ID NO: 1. The antibody specifically binding to the WRS protein in the present invention may preferably be an antibody that specifically binds to a protein having the amino acid sequence represented by SEQ ID NO: 1. The diagnostic composition of the present invention comprising the WRS-specific antibody as an agent for measuring the expression level of WRS may further include a preparation necessary for a conventional method for detecting proteins, and may be used to measure the level of the WRS protein in a subject using unlimitedly a method known in the art for detecting known proteins.

Meanwhile, when the diagnostic composition of the present invention is to measure the expression level of WRS mRNA, the agent for measuring the WRS mRNA expression level may be a probe or a primer set that specifically binds to WRS mRNA.

The WRS mRNA may be derived from a mammal including a human, and preferably may be including the mRNA sequence represented by SEQ ID NO: 2 of human WRS. The diagnostic composition of the present invention, which comprises an agent for measuring the expression level of WRS by a probe or a primer set specific to WRS mRNA, may further comprise a preparation necessary for a conventional method method for detecting RNA. Methods for detecting known RNA using this composition can be used without limitation to determine the level of WRS mRNA in a subject.

A 'primer' is a short single strand oligonucleotide that acts as a starting point for DNA synthesis. The primer specifically binds to a polynucleotide as a template under a suitable buffer and temperature conditions, and DNA is synthesized by the addition of nucleoside triphosphate having a base complementary to the template DNA by the DNA polymerase. The primer is generally composed of 15 to 30 nucleotide sequences, and the melting temperature (Tm) varies depending on the base structure and the length.

The sequence of the primer does not need to have a sequence completely complementary to a partial nucleotide sequence of the template, and it is sufficient that the complementary nucleotide has sufficient complementarity within a range capable of hybridizing with the template and acting as a primer. Therefore, the primer for measuring the expression level of WRS mRNA in the present invention does not need to have a sequence completely complementary to the WRS gene sequence, but it is sufficient that the specific length of the WRS mRNA or WRS cDNA is amplified through DNA synthesis to have a length and complementarity to the purpose of measuring the amount of WRS mRNA. The primer for the amplification reaction is composed of a set (pair) complementarily binding to a template (or sense) and an opposite region (antisense) at ends of a specific region of the WRS mRNA to be amplified, respectively. Primers can be easily designed by those skilled in the art with reference to the WRS mRNA or cDNA sequence.

The primer of the present invention is preferably one set or one pair which specifically binds to the nucleotide sequence of WRS mRNA represented by SEQ ID NO: 2, most preferably the primer set represented by the nucleotide sequence of SEQ ID NO: 3 and SEQ ID NO: 4.

A "probe" refers to a fragment of a polynucleotide, such as RNA or DNA having a base pair length of several to several hundreds, which can specifically bind to mRNA or cDNA (complementary DNA) of a specific gene. Also, the probe is labeled so that the presence or expression level of mRNA or cDNA to be bound can be confirmed. For the purpose of the present invention, a probe complementary to WRS mRNA can be used for the diagnosis of infectious inflammatory disease by measuring the expression level of WRS mRNA through performing hybridization with a sample of a subject. The selection and hybridization conditions of the probes can be appropriately selected according to techniques known in the art.

The primer or probe of the present invention can be chemically synthesized using a phosphoramidite solid support synthesis method or other well-known methods. In addition, the primer or probe may be modified in various ways according to methods known in the art, so long as it does not interfere with hybridization with WRS mRNA. Examples of such modifications include, but are not limited to, methylation, capping, substitution with one or more of the natural nucleotide analogs and modifications between nucleotides such as uncharged linkers (e.g., methylphosphonate, phosphotriester, phosphoramidate, and carbamate) or charged conjugates (e.g., phosphorothioate, and phosphorodithioate), and the combination of labeling material using fluorescence or enzymes.

In the present invention, infection refers to the infiltration of one or two or more kinds of foreign bacteria (including bacteria, gram-negative bacteria or gram-positive bacteria), viruses and fungi into the body to settle, multiply, and parasitize. The infectious diseases can be any disease caused by a reaction in a living body as a result of an infection of a pathogen. Responses resulting from infectious diseases can include inflammation, pain, fever, fatigue, edema, and hypotension. Preferably, the infectious disease of the present invention include *salmonellosis*, food poisoning, typhoid, paratyphoid, pneumonia, pulmonary tuberculosis, tuberculosis, sepsis, septic shock, urinary tract infection, cystitis, pyelonephritis, urethritis, prostatitis, upper respiratory tract infection, otitis media, and more preferably *salmonellosis*, food poisoning, pneumonia, sepsis, and septic shock.

In the present invention, the sepsis is a systemic inflammatory reaction syndrome which is a complication of an infectious disease. When the cause of the sepsis cannot be diagnosed quickly and accurately, it becomes fetal diseases that causes death, including severe septicemia, septic shock, multiple organ dysfunction syndrome (MODS) resulting in dysfunctions such as lung, kidney, liver, and circulatory system, disseminated intravascular coagulation (DIC), acute respiratory distress syndrome (ARDS), or acute kidney injury (AKI).

As used herein, sepsis includes sepsis associated with the final stage of sepsis, severe sepsis, septic shock and multiple organ dysfunction syndrome (MODS), disseminated intravascular coagulation syndrome (DIC), acute respiratory distress syndrome (ARDS), or acute kidney injury (AKI) associated with sepsis, but is not limited to.

The present invention also provides a kit for diagnosing an infectious disease, the kit comprising an agent for measuring the protein or mRNA expression level of tryptophanyl-tRNA synthetase.

The diagnostic kit of the present invention may include one or more other component compositions, solutions or devices suitable for the assay method as well as an antibody selectively recognizing the WRS protein as a marker or primers and probes recognizing WRS mRNA as a marker.

In a specific embodiment, the diagnostic kit may be a diagnostic kit comprising essential elements necessary for performing a reverse transcription polymerase chain reaction (RT-PCR). The RT-PCR kit contains a pair of specific primers for the marker gene. The primer is a nucleotide having sequence specific to the nucleic acid sequence of each marker gene, and is about 7 bp to 50 bp in length, more preferably about 10 bp to 30 bp in length. It may also contain a primer specific for the nucleic acid sequence of the control gene. Other RT-PCR kits consist of test tubes or other appropriate containers, reaction buffers (pH and various magnesium concentrations), deoxynucleotides (dNTPs), enzymes such as Taq polymerase and reverse transcriptase, DNAse, RNAse inhibitor DEPC Water (DEPC-water), and sterile water.

Another aspect of the present invention may be a diagnostic kit characterized by including essential elements necessary for performing a DNA chip. The DNA chip kit may consist of a board on which a cDNA or oligonucleotide corresponding to a gene or a fragment thereof is attached, and reagents, preparations, and enzymes for producing a fluorescent-labeled probe. The board may also comprise a cDNA or oligonucleotide corresponding to a control gene or fragment thereof. Most preferably, it may be a diagnostic kit characterized by comprising essential elements necessary for performing an ELISA. ELISA kits contain antibodies specific for the marker protein. Antibodies include monoclonal antibodies, polyclonal antibodies or recombinant antibodies with high specificity and affinity for each marker protein and little cross reactivity to other proteins. The ELISA kit may also include antibodies specific for a control protein. Other ELISA kits include reagents capable of detecting bound antibodies, such as labeled secondary antibodies, chromophores, enzymes (in conjugated form with antibodies) and their substrates or other substance capable of binding to the antibody. In addition, the kit of the present invention removes the substrate to be color-developed with the enzyme and the unbound protein, and may include a washing solution or an eluting solution that can only retain the bound protein markers.

The sample used for the analysis includes a biological sample capable of identifying an infectious inflammatory disease-specific protein that can be distinguished from a healthy state such as blood, serum, urine, leakage, and saliva. Preferably it can be measured from biological liquid samples, such as blood, serum, and plasma. The sample may be prepared to increase the detection sensitivity of the protein marker. For example, the serum sample obtained from the patient can be pretreated using methods such as anion exchange chromatography, affinity chromatography, size exclusion chromatography, liquid chromatography, sequential extraction or gel electrophoresis.

The present invention also provides a method for detecting tryptophanyl-tRNA synthetase in a subject in need of obtaining information necessary for the diagnosis of an infectious disease, the method comprises:
 (a) providing a sample of a subject;
 (b) measuring the expression level of tryptophanyl-tRNA synthetase in the sample; and
 (c) comparing the level of tryptophanyl-tRNA synthetase in the subject with the level of a healthy subject, and determining that the subject having an increased expression level of tryptophanyl-tRNA synthetase compared to the healthy subject has been infected with the infectious disease.

The inventors first discovered that the WRS can function as a marker of a new infectious disease and provided a method for measuring the expression level of the WRS to provide information necessary for diagnosis of an infectious disease. Hereinafter, the method of the present invention will be described.

(a) of the method of the present invention is to provide a sample of a test object.

The sample can be used without limitation as long as it is collected from a subject to be diagnosed as having an infectious disease. For example, the sample can be a cell or tissue, blood, whole blood, serum, plasma, saliva, cerebrospinal fluid, various secretions, urine, and feces obtained by biopsy. Preferably blood, plasma, serum, saliva, nasal mucus, sputum, capsular fluid, amniotic fluid, ascites, cervix or vaginal discharge, urine and cerebrospinal fluid. Most preferably blood, plasma, or serum.

(b) of the method of the present invention is to measure the expression level of the WRS in the sample provided in (a). The level of expression of the WRS may be the level of expression of WRS protein or WRS mRNA.

The level of WRS protein can be detected or measured using an antibody that specifically binds to the WRS protein. The WRS protein-specific antibody is as described in the diagnostic composition of the present invention.

Methods known in the art for measuring the expression level of the WRS protein can be used without limitation, and examples thereof include Western blotting, dot blotting, enzyme linked immunosorbent assay (ELISA), radioimmunoassay (RIA), radioimmunodiffusion, ouchterlony immunodiffusion, rocket immunoelectrophoresis, immunohistostaining, immunoprecipitation assay, complement fixation assay, FACS, and protein chip, but are not limited thereto. Preferably, an ELISA method can be used.

The WRS mRNA level can be determined by amplifying the mRNA or cDNA of the WRS from a sample of the subject using a primer set or a probe that specifically binds to WRS mRNA or by using hybridization with a probe to amplify WRS mRNA in a sample of the subject. The primers and probes of the WRS are the same as described in the diagnostic composition of the present invention. The measurement of the expression level of WRS mRNA can be performed by methods known in the art without any limitations. For example, reverse transcription polymerase chain reaction (RT-PCR), competitive RT-PCR, real-time RT-PCR, RNase protection assay (RPA), northern blotting, DNA microarray chip, RNA sequencing, hybridization using nanostring, and in situ hybridization of tissue sections, but are not limited thereto.

(c) of the method of the present invention is to compare the level of tryptophanyl-tRNA synthetase in the subject with the level of a healthy subject, and determining that the subject having an increased expression level of tryptophanyl-tRNA synthetase compared to the healthy subject has been infected with the infectious disease.

The level of expression of the WRS of the subject measured by the method of (b) described above is compared with the WRS level of the healthy person measured by the same method. If the level of WRS expression is increased compared to a normal healthy person, the subject is determined to have an infectious disease. In addition, if the infectious disease is sepsis, the higher the level of WRS expression is, the more severe the sepsis may be. As to the degree of increase in the level of WRS expression that is the basis of diagnosis, the correlation between the expression level of the WRS and the severity of sepsis is analyzed according to the technique known in the art for the method of measuring the selected WRS expression level, and appropriate diagnostic criteria may be provided to indicate severity of sepsis depending on the range of WRS expression levels. In an embodiment of the present invention, it has been shown to have a close correlation that the higher the level of expression of WRS is, the higher the degree of severity of sepsis is by using various indicators such as severe sepsis, septic shock, SOFA score, and the survival after 28 days of diagnosis of sepsis.

In one embodiment of the present invention, the amount of the WRS expressed in the serum of the dead patients was significantly increased in the investigator's clinical test as compared with that in the surviving patients. It was confirmed that this was indistinguishable from the conventionally used marker, procalcitonin.

Accordingly, the present invention provides a composition for determining the mortality risk of an infectious disease, the composition comprising an agent for measuring the protein or mRNA expression level of tryptophanyl-tRNA synthase.

In the present invention, the mortality risk refers to the infectious disease mortality risk. Death due to infection shows some or all symptoms of inflammation, high fever, pain, dyspnea, hypothermia, and hypotension, and it means that death is caused by shock, partial or multiple organ failure.

In addition, the present invention provides a method for determining the mortality risk of a subject afflicted with an infectious disease, the method comprising:
 (a) providing a sample of a subject;
 (b) measuring the expression level of tryptophanyl-tRNA synthetase in the sample; and
 (c) determining that the mortality risk of the subject increases proportionally to an increase in the level of tryptophanyl-tRNA synthetase.

Samples in the discrimination method of the present invention are as described above.

The present invention provides the use of an agent for measuring the protein or mRNA expression level of tryptophanyl-tRNA synthetase for preparing an agent for the diagnosis of an infectious disease.

The present invention provides a method for diagnosing an infectious disease in a subject in need thereof, the method comprising measuring the protein or mRNA expression level of tryptophanyl-tRNA synthetase in a sample of a subject in need thereof.

The present invention provides a use of an agent for measuring the protein or mRNA expression level of tryptophanyl-tRNA synthetase for preparing an agent for determining the mortality risk of a subject afflicted with an infectious disease.

The subject of the present invention may be an animal, preferably an animal including a mammal, particularly a human, and more preferably a human or a patient, who needs diagnosis.

In the present invention, the method of diagnosing the infectious disease is to compare the level of the WRS of the test sample measured with that of a healthy person, and to determine that the subject having increased WRS expression level compared to a healthy person is infected with the disease. The comparison with such a healthy person is as described above.

The term "comprising" of the present invention is used synonymously with "containing" or "characterized" and does not exclude additional components or method not mentioned in the composition or method. The term "consisting of" excludes additional elements, steps or components not otherwise mentioned. The term "essentially consisting of" means substances or steps which do not substantially affect its basic properties in addition to the mentioned substances or steps in the context of the composition or method.

Advantageous Effect

Therefore, according to the present invention, the present invention, the WRS is increased only in infection-induced inflammatory diseases, differentiating non-infectious diseases therefrom, and is rapidly increased in the early stage of infection. In addition, the level of the WRS is closely correlated with the severity and prognosis of diseases or complications induced by infection. Therefore, the WRS can be used as a marker for more rapid and accurate diagnosis, in comparison to a conventional marker for infectious diseases or complications thereof.

BRIEF DESCRIPTION OF THE DRAWINGS

FIG. 2 A shows the time course of WRS levels present in the culture medium of peripheral blood mononuclear cells (PBMC) infected with RSV (MOI=2) or PRS virus (MOI=2).

FIG. 2 B shows ELISA results of measuring the level of the WRS present in the serum of a healthy (HC, n=20) and viral pneumonia (n=5) patient. The statistical significance uses the Mann Whitney test, and the p value denoted by * is 0.04.

FIGS. 3 B and C show ELISA results of measuring the levels of GRS or KRS present in the serum of healthy controls (HC) and sepsis patients, respectively (Statistical significance in the FIG. 3A was determined by Dunn's comparison test after Kruskal wallis test. FIGS. 3 B and C were determined by the two-tailed Mann-Whitney test. *** indicates p<0.001, * indicates p<0.05, n.s indicates statistically not significant.).

FIGS. 4 B and C show ELISA results of measuring the levels of GRS or KRS present in the serum of healthy controls (HC) and sepsis patients, respectively (statistical significance was determined by the two-tailed Mann-Whitney test. *** indicates p<0.001, * indicates p<0.05, ns indicates statistically not significant).

FIG. 5 B shows ELISA results of measuring the levels of the WRS present in the serum of single infected and multiple infected patients (statistical significance was determined by Dunn's comparison test after Kruskal wallis test. *** indicates p<0.001, * indicates p<0.05, ns indicates statistically not significant).

MODE FOR CARRYING OUT INVENTION

Figure 1:
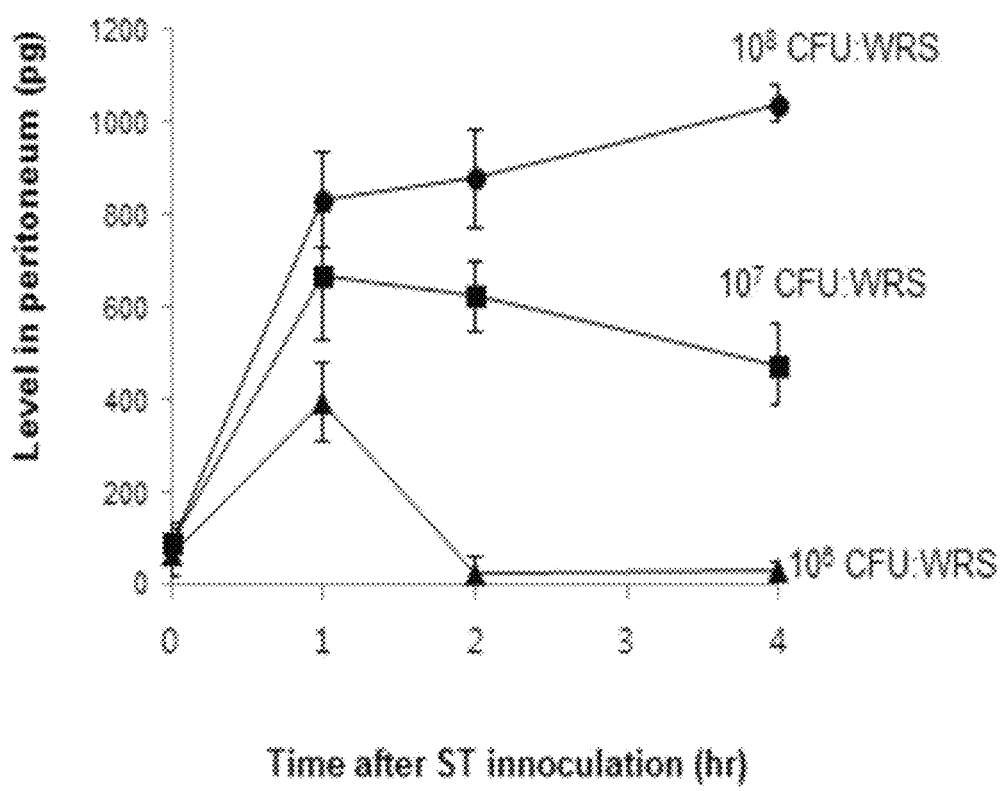
FIG. 1 shows the change of WRS with time after infection measured by ELISA in peritoneal lavage fluid of mice injected intraperitoneally with $10^8$, $10^7$ or $10^8$ CFU of *S. typhimurium* (ST). The abscissa represents the time at which the abdominal exudate was obtained after ST infection (Time after ST inoculation (hr.))

Hereinafter, the present invention will be described in detail.

However, the following examples are illustrative of the present invention, and the present invention is not limited to the following examples.

Clinical Experiment

The experimental method was conducted under permission of the institutional review board in Seoul National University (Permit No. 1502-001-010). Serum samples from healthy controls were collected at the Seoul National University Health Center. Serum samples from 99 sepsis patients were obtained through severe sepsis or septic shock intensive care unit. The patients who provided the serum used in the experiment were those who were admitted to the intensive care unit (ICU) of the university—affiliated hospital in Seoul. Only the patients who had confirmed the bacterial infection participated in the experiment. The diagnosis of severe sepsis or septic shock was made according to the ACCP/SCCM consensus conference (1992). The experiment was conducted with the informed consent of all patients participating in the experiment according to the policy of the review committee. The experiment was also approved by the Review Committee of Asan Medical Center in Seoul. Between January 2014 and July 2015, a total of 35 patients admitted to the Seoul Severance Hospital allergy-asthma clinic participated in the experiment. The experiment included 26 healthy controls and 35 stable asthmatics diagnosed with asthma based on the results of symptoms and pulmonary function tests (more than 12% increase in forced expiratory volume for 1 second (FEV1) after the used of bronchodilator) by an allergist. The stable asthma was defined as asthmatic patients who maintained the usual dose of the drug without increasing the drug administration for the past one month. Clinical trials were approved by Severance Hospital and Yonsei University Health System (Permission No. 4-2013-0397). The serum was collected from 42 patients with primary Sjogren's syndrome (pSS), 35 patients with rheumatoid arthritis (RA), and 20 healthy controls. Primary Sjogren's syndrome was diagnosed according to American-European Consensus Group criteria for pSS or 2012 American College of Rheumatology criteria. Rheumatoid arthritis was diagnosed according to the 1987 revised criteria for classification of rheumatoid arthritis or 2010 rheumatoid arthritis classification criteria. According to the principle of the Helsinki Declaration, all patients and healthy controls participating in the experiment received informed consent from the experiment. The experiment was approved by the Seoul St. Mary's Hospital Review Committee (KC13ONMI0646).

Clinical Experiment—Comparison with Procalcitonin

Based on the review committee's policy of each institution, informed consent was obtained on all patients who participated in the experiment including 120 healthy persons, 18 SIRS patients (due to causes other than infectious diseases), 166 sepsis patients and 160 septic shock patients. The systemic inflammatory response syndrome (SIRS), septicemia, and septic shock which were obtained from patients admitted to the ICU of Seoul National University Hospital were diagnosed according to the ACCP/SCCM consensus conference (1992).

Levels of procalcitonin (RayBiotech, USA Cat No: ELH-PROCALC) and WRS (CUSABIO, China, Cat No: CSB-E11789h) in serum were measured using ELISA kits.

Cell Culture

Human peripheral blood mononuclear cells (PBMC) were isolated using Cell Preparation Tube (CPTTM, Becton Dickinson) containing sodium citrate.

Bacterial Strain and Infection

*Salmonella typhimurium* (ATCC 14028) was obtained from the Center for Microbial Conservation, Seoul, Korea. Bacteria were routinely cultured using nutrient broth of BD bioscience. Bacteria were incubated overnight before infection and were obtained at a density of $1 \times 10^8$ CFU. Bacterial density was estimated using absorbance and calibration curve at 600 nm. For PBMC or mouse infection experiments, the bacteria were washed with PBS and redispersed in serum-free medium or PBS.

Enzyme-Linked Immunosorbent Assay, ELISA

For quantitative analysis of the WRS and KRS of mouse and human, the amount of protein secreted in culture medium or serum was measured by ELISA kit. The WRS ELISA kit was purchased from Cusabio (Wuhan, China, catalog number CSB-E11789h) and KRS was purchased from USCN (Wuhan, China, catalog number SED002 Hu).

Statistics

Statistical significance was determined when the provability value (p-value) was less than 0.05. All statistical calculations were performed using Graphpad prism 5.0 (GraphPad Software).

Example 1

Increased WRS Levels Due to Bacterial or Viral Infection

<1-1> WRS Secretion by *Salmonella* Infection

*Salmonella* typimurium was injected into mouse abdominal cavity to confirm the amount of WRS present in the peritoneal exudate.

*Salmonella* of $10^6$, $10^7$ or $10^8$ CFU was intraperitoneally injected into female C57B116 at 9-10 weeks old, and peritoneal exudate was obtained from 5 to 11 mice every hour up to four hours after the bacterial infection to measure the amount of WRS present in the peritoneal exudate by ELISA (FIG. 1). WRS secreted by peritoneal exudate was secreted from the very early stage after *salmonella* infection and increased according to *salmonella* concentration. The amount of WRS was almost reached at 1 hour after infection.

<1-2> Secretion of WRS Due to Viral Infection

In addition to bacteria, we examined the secretion of WRS by viral infection by using serum of human peripheral blood mononuclear cells and viral pneumonia.

Figure 2:
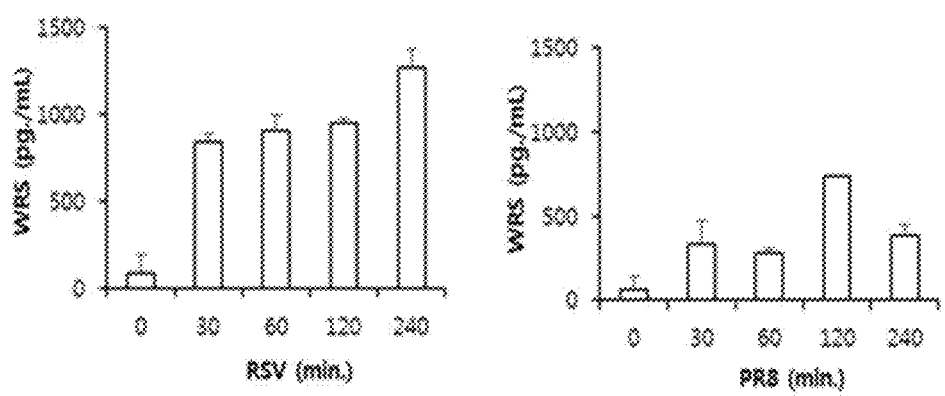
FIG. 2 shows ELISA test results for measuring the manner of WRS secretion following viral infection.
Figure 2:
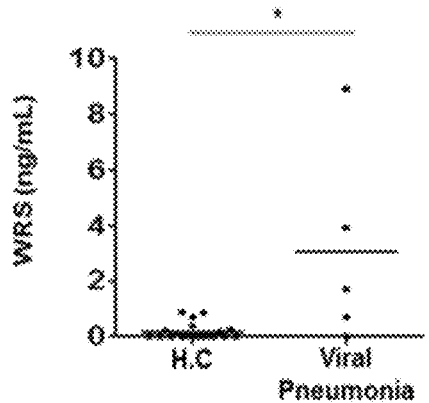

When human peripheral blood mononuclear cells (PBMC) are infected with respiratory syncytial virus (RSV) and PR8 virus such as influenza virus, the WRS was significantly increased in the cell culture medium from 30 minutes after infection, and it was confirmed that the level of secreted WRS was maintained by 4 hours after infection in which the experiment was conducted (A in FIG. 2). In addition, it was confirmed that the amount of WRS was significantly increased in the serum of patients with viral pneumonia compared with the healthy controls (H.C) (B in FIG. 2)

These results show that the level of WRS is increased by viral infection.

Example 2

WRS-Specific Secretion in Infectious Inflammatory Disease

<2-1> Increase in WRS in Sepsis and Septic Shock Patients

The level of WRS in patients with septicemia and septic shock due to infection was compared with healthy controls.

The sepsis patients who participated in this experiment were patients with severe sepsis and septic shock who were admitted to the ICU of Asan Medical Center in Seoul. Bacteria and fungi detected in the patients are as described in Table 1.

Figure 3:
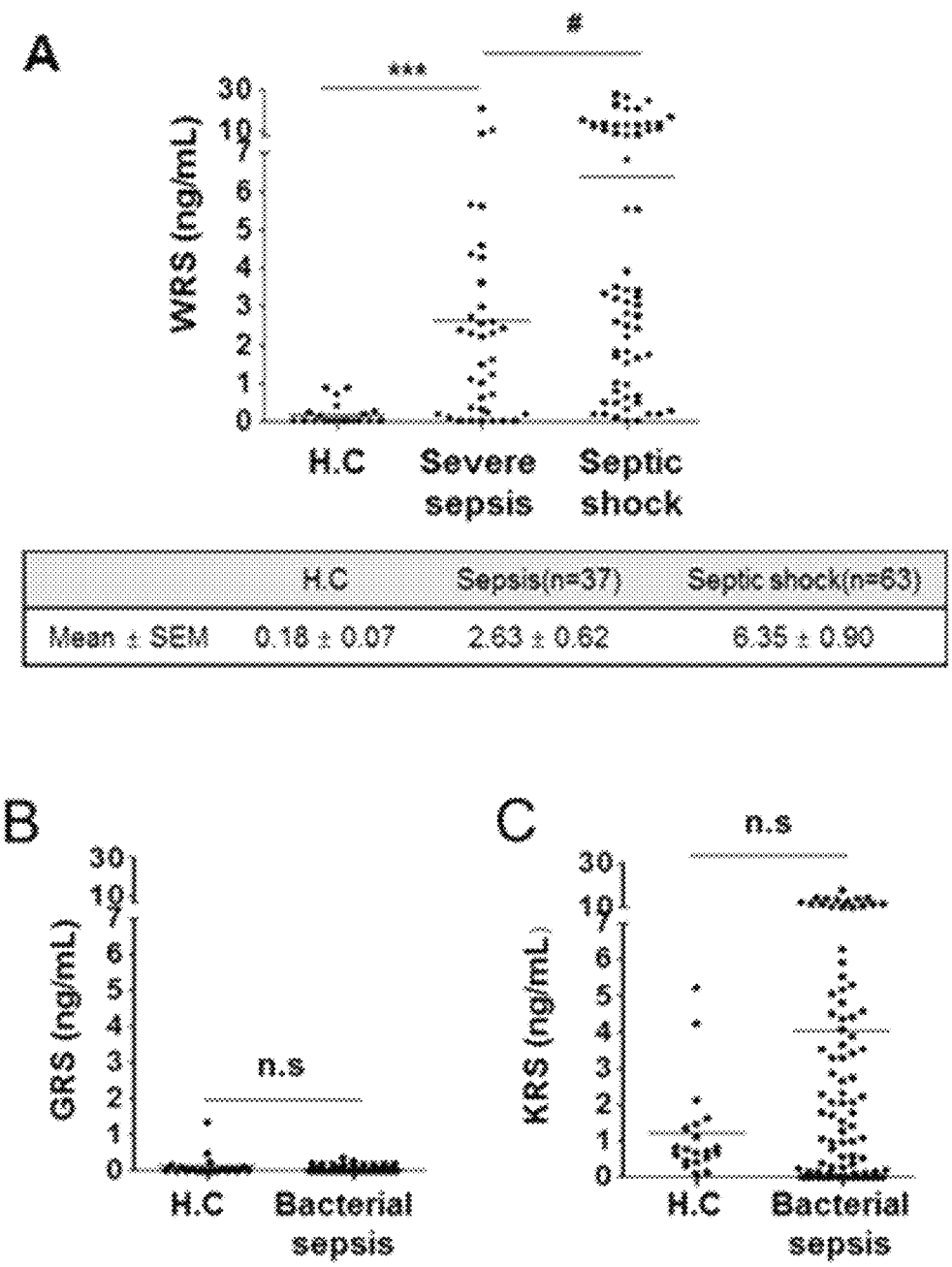
FIG. 3 A shows ELISA results of measuring the level of the WRS present in the serum of healthy control (H.C), severe sepsis, and septic shock patients.

The levels of WRS were significantly increased in the severe sepsis patients and septic shock patients compared to healthy controls (H.C) (FIG. 3A). The measured WRS values were increased by about 20 times in 2.63±0.62 ng/ml (n=37) patients with septic patients compared with 0.18±0.06 ng/ml (n=20) in the healthy controls. In addition, the WRS level in patients with septic shock was 6.35±0.90 ng/ml (n=63), which was about 50 times higher than that of the healthy controls. The WRS level in patients with septic shock is much higher than that in patients with severe sepsis, indicating that the level of WRS is closely related to the severity of sepsis.

In contrast to the significant increase in WRS levels in patients with sepsis compared with healthy controls, glycyl-tRNA synthetase (GRS) and lysyl-tRNA synthetase (KRS) such as aminoacyl tRNA synthetase (ARS) secreted into different types showed no significant changes (FIGS. 3B and 3C).

TABLE 1

| Gram (−) bacteria | N | Gram (+) bacteria | N | Multi-infection | N | Fungi | N |
|---|---|---|---|---|---|---|---|
| Acinetobacter baumanii | 1 | Enterococcus faecalis | 2 | CRAB, E. coli | 1 | Candida albican | 2 |
| Acinetobacter baumanii (CRAB) | 7 | Enterococcus faecalis (VRE) | 1 | CRAB, P. mirabilis | 1 | Candida galabrata | 1 |
| Acinetobacter baumanii (CSAB) | 2 | Staphylococcus aureus (MRSA) | 14 | K. pneumonia, Citrobacter | 1 | Bowel perforcandida tropicalis | 1 |
| Aeromona hydrophila | 3 | Staphylococcus aureus (MSSA) | 3 | K. pneumonia, E. coli | 1 | Aspergillus | 3 |
| Burkholderia cepacia | 2 | Staphylococcus epidermidis | 1 | K. pneumonia, A. baumanii (CRAB) | 1 | | |
| Enterobacter aerogenes | 1 | Streptococcus pneumoniae | | 3 K. pneumonia, P. aeruginosa | 1 | | |

TABLE 1-continued

| Gram (−) bacteria | N | Gram (+) bacteria | N | Multi-infection | N | Fungi | N |
|---|---|---|---|---|---|---|---|
| *Enterobacter cloacae* | 1 | *Streptococcus agalactiae* | 1 | *E. Coli, P. aerunginosa* (CSPA) | 1 | | |
| *Escherichia coli* | 21 | | | MRSA, *A. baumanii* | 1 | | |
| *Haemophilus Influenza* | 1 | | | MRSA, ESBL, *Serratia* | 1 | | |
| *Klebsiella pneumonia* | 13 | | | *Enterococcus, Bacteriodes, Streptococcus* | 1 | | |
| *Morganella morganii* | 1 | | | Fungus + MRSA | 1 | | |
| *Proteus mirabilis* | 1 | | | unknown | 3 | | |
| *Stenotrophomonas maltophilia* | 1 | | | | | | |
| *Pseudomonas aeruginosa* (CRPA) | 1 | | | | | | |
| *Pseudomonas fluorescens* | 4 | | | | | | |
| *Vibrio vufnificus* | 2 | | | | | | |

Figure 4:
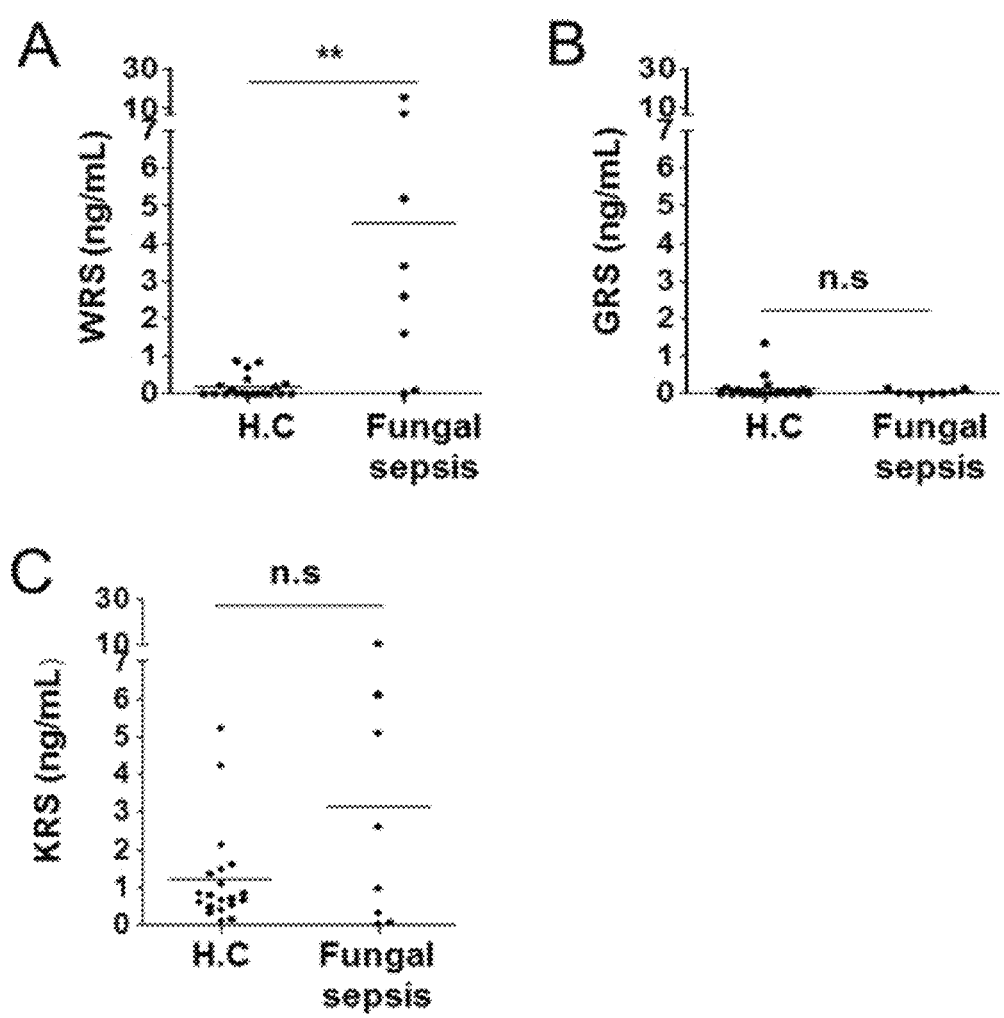
FIG. 4 A shows ELISA results of measuring the level of the WRS present in the serum of healthy controls (H.C.) and fungi infected sepsis patients.

Meanwhile, as shown in FIG. 4, the levels of WRS were increased (n=8, 4.52±1.83 ng/mL, Mann-Whitney test) in serum of patients with bacterial infections as well as fungi sepsis. The serum levels of GRS and KRS were not significantly changed.

Figure 5:
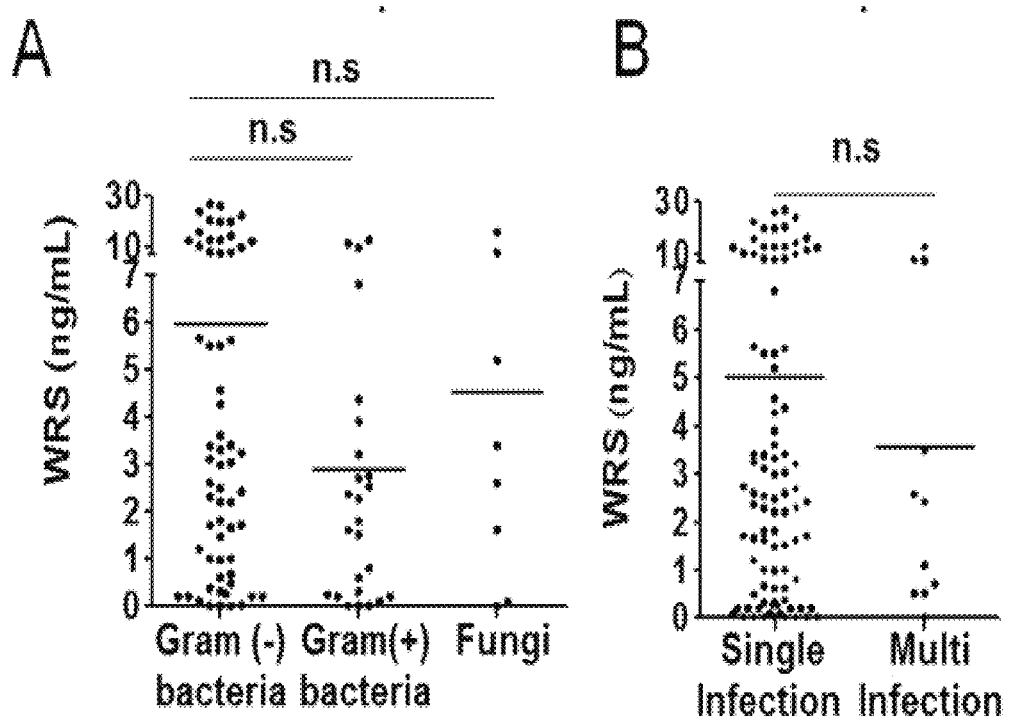
FIG. 5 A shows ELISA results of measuring the levels of the WRS present in the serum of patients with gram-positive bacterial infection and patients with fungal infection.

Among the above sepsis patients, no significant difference was observed between Gram-negative bacterial infection patients (n=62, 5.98±0.93 ng/mL), Gram-positive bacterial infection patients (n=25, 2.87±0.72 ng/mL), and fungal infection patients (n=8, 4.52±1.83), and no significant differences were observed between patients with multiple pathogens (n=11, 3.53±1.22 ng/mL) and those with single pathogens (n=94, 5.01±0.67 ng/mL) (FIG. 5).

<2-2> WRS Level in Non-Infectious Inflammatory Disease

The levels of WRSin patients with non-infectious inflammatory response syndrome (systemic inflammatory response syndrome, SIRS), asthma such as sterile chronic inflammatory diseases, rheumatoid arthritis, and Sjogren's syndrome were compared with healthy controls.

Figure 6:
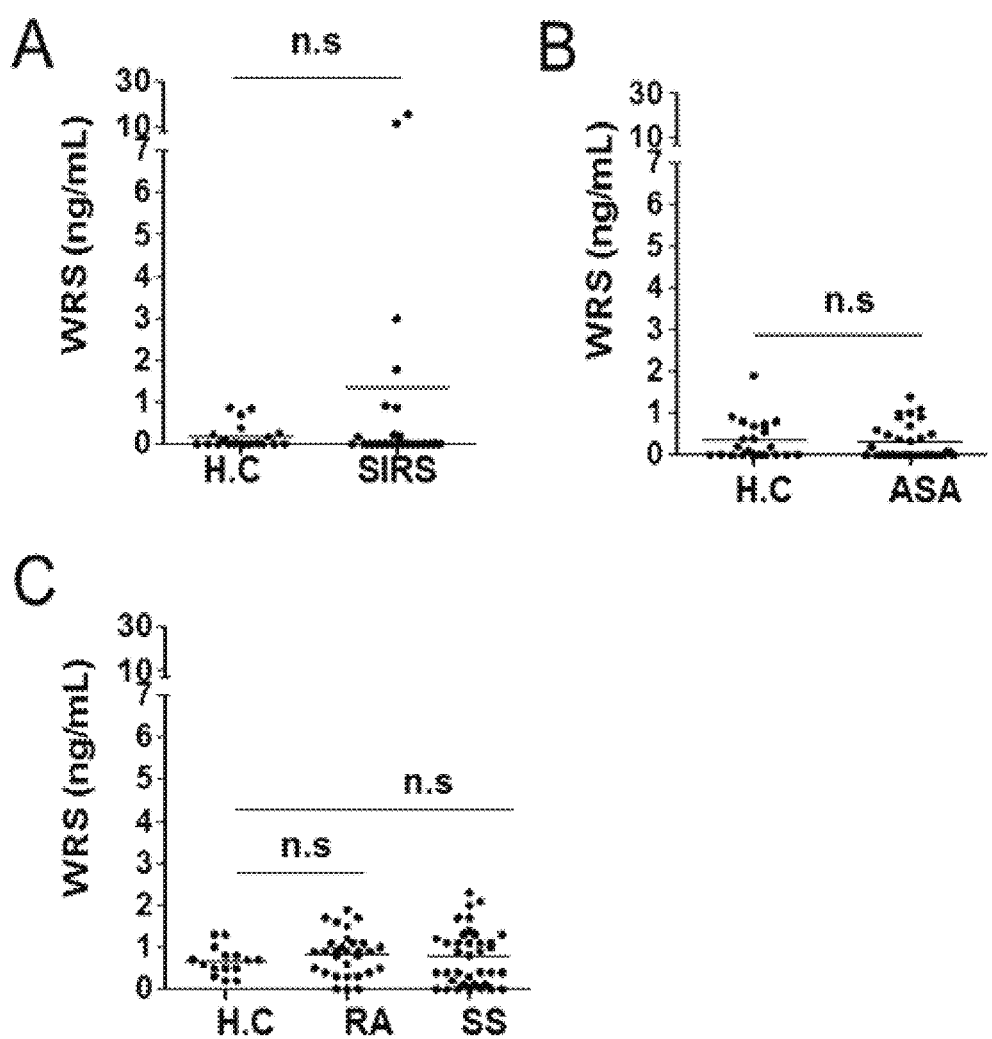
FIG. 6 is a graph showing the results of the level of the WRS in patients with a systemic inflammatory response syndrome (SIRS, FIG. 6 A), asthma (ASA, FIG. 6 B) such as sterile chronic inflammatory diseases, rheumatoid arthritis (RA, FIG. 6 C) and Sjogren's syndrome (SS, FIG. 6 C) compared to a healthy controls (HC).

The levels of WRSpresent in the serum of these non-infectious inflammatory disease patients were not significantly different from healthy controls (FIG. 6). The WRS detected in the serum of systemic inflammatory response syndrome (FIG. 6A), asthmatic patients (FIG. 6B), rheumatoid arthritis patients (FIG. 60), and Sjogren's syndrome patients (FIG. 6C) was no statistically significant difference.

Example 3

Efficiency of WRS as a Diagnostic Marker of Infectious Inflammatory Diseases

<3-1> Performance of WRS as an Infectious Inflammatory Disease Marker

In order to confirm the performance of WRS as an infectious inflammatory disease marker, a receiver operating characteristic curve (ROC curve) was prepared.

Figure 7:
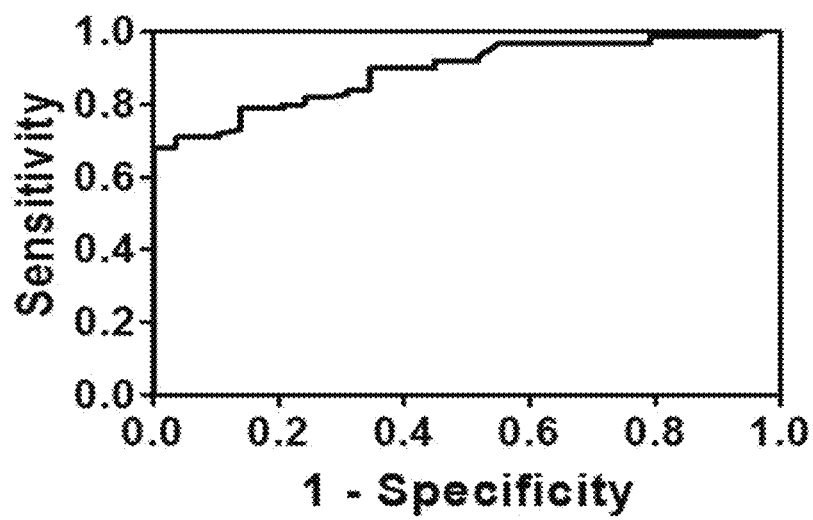
FIG. 7 shows the ROC curve of the WRS.

The AUC of the WRS on the ROC curve of 100 patients with bacterial infected sepsis was 0.90 (p<0.0001), the cut off value was 0.28 ng mL, the sensitivity was 82% and the specificity was 80% (FIG. 7).

<3-2> Correlations Among Level of WRS, Infectious Inflammatory Disease Severity and Prognosis To further confirm the performance of WRS as an infectious inflammatory disease marker, we examined the correlations among the level of WRS, the severity of sepsis and the prognosis of sepsis.

Figure 8:
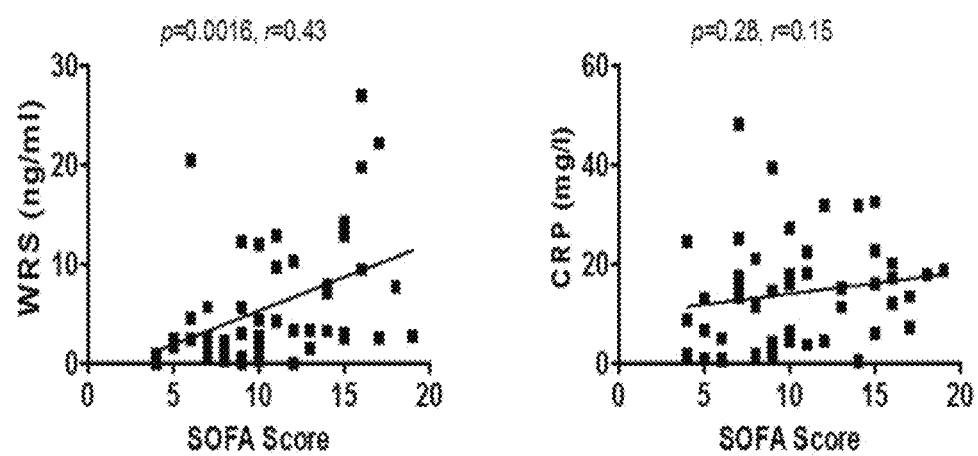
FIG. 8 shows a graph showing the correlation between the WRS and the SOFA score of the CRP. r is a Pearson correlation coefficient, and p is a probability value.

The sequential organ failure assessment score (SOFA score), which indicates the prognosis of sepsis patients, and the level of WRS or CRP detected in the patient's serum were shown as a graph, and the Pearson correlation coefficient is calculated (FIG. 8).

The Pearson correlation coefficient of WRS was 0.43, which was significantly higher than that of CRP of 0.15, and statistically significant correlation was shown. In other words, the level of WRS is more closely correlated with the SOFA score of patients with sepsis than the CRP, which is an existing inflammation index.

Figure 9:
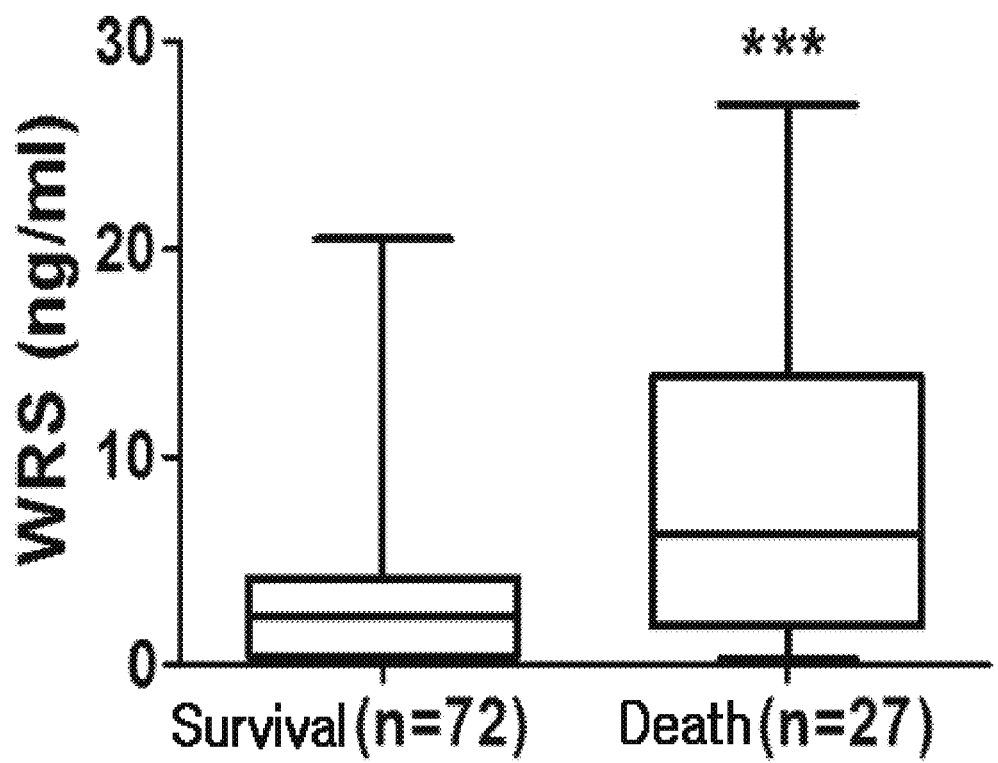
FIG. 9 shows the WRS levels of patients who survived and died after 28 days of sepsis diagnosis. Mann Whitney test is used for statistical significance, and the p value indicated *** is 0.0007.

In addition, the survival and the level of WRS after 28 days of the diagnosis of sepsis were measured as other indicators of the prognosis of sepsis patients, and statistical significance was determined by the Whitney test (FIG. 9). There was a statistically significant difference in WRS levels among patients who died after 28 days of the diagnosis of sepsis (death, n=27, WRS 9.14+1.63 ng/ml, survival, n=72, WRS 3.36+0.49 ng/ml). Thus, the higher the WRS level was, the worse the survival prognosis of sepsis was.

Example 4

Comparison with Procalcitonin

<4-1> Comparison of Contents in Serum

The amount of WRS (CUSABIO, China, Cat No: CSB-E11789h) and procalcitonin (RayBiotech, USA Cat No: ELH-PROCALC) known as major inflammatory markers in serum of 120 healthy subjects, 18 SIRS patients (due to non-infectious cause), 166 sepsis patients and 160 septic shock patients was quantitatively determined by ELISA method according to the manufacturer's instructions.

As a result of Table 2, procalcitonin was distinguished from non-infectious systemic inflammatory symptom SIRS in comparison with healthy persons and a more amount of it was detected in sepsis or septic shock, which is a complication of infectious disease. However, WRS was found to be specific only for complications of infectious diseases.

TABLE 2

Comparison of WRS and Procalcitonin in healthy Controls and Patients

| Classification | Healthy controls (n = 120) | SIRS (n = 18) | Sepsis (n = 166) | Septic shock (n = 160) | P value |
|---|---|---|---|---|---|
| WRS (ng/mL) | 0.06 ± 0.02 | 0.20 ± 0.12 | 1.29 ± 0.20 | 6.78 ± 0.79 | 0.000 |
| Procalcitonin (ng/mL) | 0.03 ± 0.01 | 1.02 ± 0.36 | 2.02 ± 0.23 | 2.98 ± 0.31 | 0.000 |

<4-2> Comparison of Content by Survival

Sepsis and septic shock patients were divided into survivor group and death group according to the survival after 28 days. The content of WRS and procalcitonin in patient serum of each group was quantitatively measured as in the Example <4-1> above.

As shown in the following Table 3, in the case of procalcitonin, there was no distinction between survivors and deaths, but WRS was classified as statistically meaningful, and it was confirmed that patients with the fear of death could be selected.

TABLE 3

Comparison of WRS and Procalcitonin in Survival and Death Patients

|  | Survivals | Deaths | P value |
|---|---|---|---|
| WRS (ng/mL) | 2.47 ± 0.40 | 6.22 ± 0.84 | <0.05 |
| Procalcitonin (ng/mL) | 2.29 ± 0.22 | 2.73 ± 0.35 | NS |

<4-3> Correlation Analysis with Procalcitonin

In order to confirm the correlation between the conventional diagnosis of procalcitonin and WRS, Spearman's correlation analysis was performed using WRS and procalcitonin measurements for sepsis patients.

Figure 10:
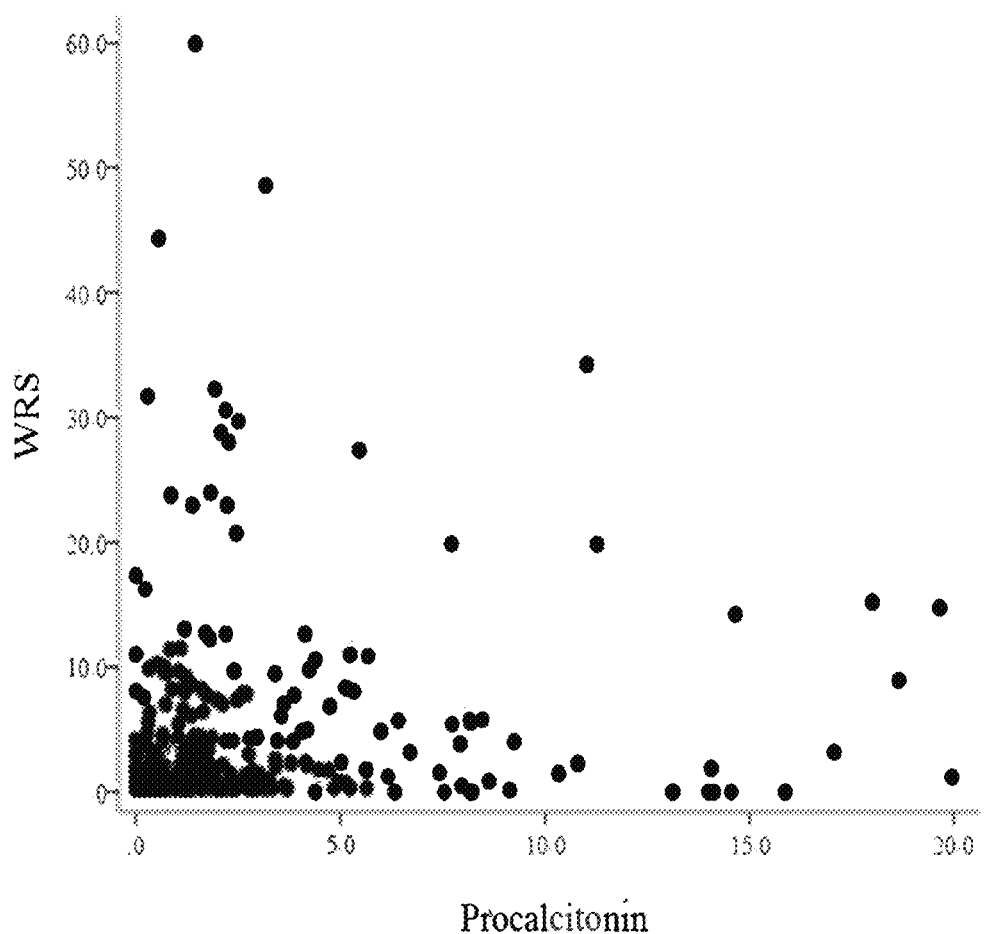
FIG. 10 confirmed the levels of the WRS and procalcitonin in serum by Spearman's association assay.

As shown in FIG. 10, it was confirmed that Spearman's rho value (r) was 0.127 and p value was 0.022 between WRS and procalcitonin.

INDUSTRIAL APPLICABILITY

As we have seen, the WRS is increased only in infection-induced infectious diseases, differentiating non-infectious diseases therefrom, and is rapidly increased in the early stage of infection. In addition, the level of the WRS is closely correlated with the severity and prognosis of diseases or complications induced by infection. Therefore, the WRS can be used as a marker for more rapid and accurate diagnosis, in comparison to a conventional marker for infectious diseases or complications thereof.

---

What is claimed is:

1. A method for diagnosing and treating sepsis or septic shock, the method comprising:

measuring a level of tryptophanyl-tRNA synthetase protein in a cell-free sample collected from a human subject suspected of suffering from sepsis or septic shock, wherein the tryptophanyl-tRNA synthetase protein comprises the amino acid sequence of SEQ ID NO: 1;

identifying the subject as having an increased level of the tryptophanyl-tRNA synthetase protein compared to the level of the tryptophanyl-tRNA synthetase protein in a cell-free sample from a healthy subject; and administering an antibiotic agent, an antiviral agent or an antifungal agent to the subject.

2. The method of claim 1, wherein the sepsis or septic shock is caused by an infection by one or more selected from the group consisting of viruses, bacteria and fungi.

3. The method of claim 2, wherein the bacteria are gram-negative bacteria or gram-positive bacteria.

4. The method of claim 1, wherein the measuring is conducted with an agent comprising an antibody that specifically binds to the tryptophanyl-tRNA synthetase protein.

5. The method of claim 1, wherein the sample is selected from the group consisting of blood, plasma, serum, saliva, nasal mucus, sputum, capsular fluid, amniotic fluid, ascites, cervical or vaginal discharge, urine and cerebrospinal fluid.

6. The method of claim 1, wherein the sample is selected plasma or serum.

* * * * *

SEQUENCE LISTING

```
<160> NUMBER OF SEQ ID NOS: 4

<210> SEQ ID NO 1
<211> LENGTH: 471
<212> TYPE: PRT
<213> ORGANISM: Homo sapiens
<220> FEATURE:
<221> NAME/KEY: MISC_FEATURE
<223> OTHER INFORMATION: human WRS protein (tryptophan-tRNA ligase,
      cytoplasmic isoform a, NP_004175.2)

<400> SEQUENCE: 1

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
```

Gln Val Leu Asp Ala Tyr Glu Asn Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
                195                 200                 205

Asp Gln Ala Tyr Ser Tyr Ala Val Glu Asn Ala Lys Asp Ile Ile Ala
210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
                260                 265                 270

Asp Cys Ile Gly Lys Ile Ser Phe Pro Ala Ile Gln Ala Ala Pro Ser
            275                 280                 285

Phe Ser Asn Ser Phe Pro Gln Ile Phe Arg Asp Arg Thr Asp Ile Gln
290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
            355                 360                 365

Lys Thr Lys Val Asn Lys His Ala Phe Ser Gly Gly Arg Asp Thr Ile
370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Asp Lys Leu Glu Gln Ile
                405                 410                 415

Arg Lys Asp Tyr Thr Ser Gly Ala Met Leu Thr Gly Glu Leu Lys Lys
                420                 425                 430

Ala Leu Ile Glu Val Leu Gln Pro Leu Ile Ala Glu His Gln Ala Arg
            435                 440                 445

Arg Lys Glu Val Thr Asp Glu Ile Val Lys Glu Phe Met Thr Pro Arg
450                 455                 460

Lys Leu Ser Phe Asp Phe Gln
465                 470

<210> SEQ ID NO 2
<211> LENGTH: 1416
<212> TYPE: DNA
<213> ORGANISM: Homo sapiens
<220> FEATURE:
<221> NAME/KEY: misc_feature
<223> OTHER INFORMATION: human WRS mRNA (tryptophanyl-tRNA synthetase
      (WARS), transcript variant 1, NM_004184.3)

<400> SEQUENCE: 2
atgcccaaca gtgagcccgc atctctgctg gagctgttca acagcatcgc cacacaaggg    60

```
gagctcgtaa ggtccctcaa agcgggaaat gcgtcaaagg atgaaattga ttctgcagta    120
aagatgttgg tgtcattaaa aatgagctac aaagctgccg cggggggagga ttacaaggct    180 gactgtcctc cagggaaccc agcacctacc agtaatcatg gcccagatgc cacagaagct    240
gaagaggatt ttgtggaccc atggacagta cagacaagca gtgcaaaagg catagactac    300
gataagctca ttgttcggtt tggaagtagt aaaattgaca aagagctaat aaaccgaata    360
gagagagcca ccggccaaag accacaccac ttcctgcgca gaggcatctt cttctcacac    420
agagatatga atcaggttct tgatgcctat gaaaataaga agccatttta tctgtacacg    480
ggccggggcc cctcttctga agcaatgcat gtaggtcacc tcattccatt tattttcaca    540
aagtggctcc aggatgtatt taacgtgccc ttggtcatcc agatgacgga tgacgagaag    600
tatctgtgga aggacctgac cctggaccag gcctatagct atgctgtgga aatgccaag    660 gacatcatcg cctgtggctt tgacatcaac aagacttttca tattctctga cctggactac    720
atggggatga gctcaggttt ctacaaaaat gtggtgaaga ttcaaaagca tgttaccttc    780
aaccaagtga aaggcatttt cggcttcact gacagcgact gcattgggaa gatcagtttt    840
cctgccatcc aggctgctcc ctccttcagc aactcattcc cacagatctt ccagacagg    900 acggatatcc agtgccttat cccatgtgcc attgaccagg atccttactt tagaatgaca    960
agggacgtcg cccccaggat cggctatcct aaaccagccc tgctgcactc caccttcttc    1020
ccagccctgc agggcgccca gaccaaaatg agtgccagcg accccaactc ctccatcttc    1080
ctcaccgaca cggccaagca gatcaaaacc aaggtcaata gcatgcgtt ttctggaggg    1140 agagacacca tcgaggagca caggcagttt ggggcaact gtgatgtgga cgtgtctttc    1200
atgtacctga ccttcttcct cgaggacgac gacaagctcg agcagatcag gaaggattac    1260
accagcggag ccatgctcac cggtgagctc aagaaggcac tcatagaggt tctgcagccc    1320
ttgatcgcag agcaccaggc ccggcgcaag gaggtcacgg atgagatagt gaaagagttc    1380
atgactcccc ggaagctgtc cttcgacttt cagtag                               1416

<210> SEQ ID NO 3
<211> LENGTH: 18
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<223> OTHER INFORMATION: human WRS forward primer (hTrpRS forward)

<400> SEQUENCE: 3
atgcccaaca gtgagccc                                                    18

<210> SEQ ID NO 4
<211> LENGTH: 24
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<223> OTHER INFORMATION: human WRS reverse primer (hTrpRS reverse)

<400> SEQUENCE: 4
ctaccctgga ggacagtcag cctt                                             24
```